United States Patent [19]

Jacques et al.

[11] Patent Number: 4,775,361
[45] Date of Patent: Oct. 4, 1988

[54] CONTROLLED REMOVAL OF HUMAN STRATUM CORNEUM BY PULSED LASER TO ENHANCE PERCUTANEOUS TRANSPORT

[75] Inventors: Steven L. Jacques, Somerville; Daniel J. McAuliffe, Revere; Irvin H. Blank, Belmont; John A. Parrish, Weston, all of Mass.

[73] Assignee: The General Hospital Corporation, Boston, Mass.

[21] Appl. No.: 851,117

[22] Filed: Apr. 10, 1986

[51] Int. Cl.$^4$ ...................... A61M 37/00; A61B 17/36
[52] U.S. Cl. .................................. 604/20; 128/303.1; 128/632
[58] Field of Search ....... 604/20; 128/303.1, 395–398, 128/632, 635

[56] References Cited

FOREIGN PATENT DOCUMENTS 0111060  6/1984  European Pat. Off. ......... 128/303.1

OTHER PUBLICATIONS

Guy et al. (1982) Clin. Res. 30 (1): 157A.
Guy et al. (1983) J. Pharm. Sci. 72 (9): 1077.
Lane et al. (1984) IBM Research Report—"Ultraviolet-Laser Ablation of Skin".
Jacques et al. (1985) Clin. Res. 33 (2): 299A.
Wolbarsht, "Laser Surgery: $CO_2$ or HF" IEEE J. Quantum Electronics, Vol. QE 20, No. 12, Dec. 1984, pp. 1427–1432.

Primary Examiner—Lee S. Cohen

[57] ABSTRACT

A method of administering a therapeutic substance to a human patient, the method having the steps of ablating the stratum corneum of a region of the skin of the patient using pulsed laser light of wavelength, pulse length, pulse energy, pulse number, and pulse repetition rate sufficient to ablate the stratum corneum without significantly damaging the underlying epidermis, and applying the therapeutic substance to the region of ablation.

8 Claims, 3 Drawing Sheets

CONTROLLED REMOVAL OF HUMAN STRATUM CORNEUM BY PULSED LASER TO ENHANCE PERCUTANEOUS TRANSPORT

BACKGROUND OF THE INVENTION

This invention realtes to percutaneous transport.

Percutaneous transport must overcome the barrier function of the stratum corneum. The barrier function generally has been overcome by one of three methods: (1) removal of the stratum corneum, as in tape stripping; (2) heating the stratum corneum, as in $CO_2$ gas monitoring; or (3) enhancement of permeability of solvents, such as DMSO and Azone.

The excimer laser produces very brief pulses of intense 193 nm ultraviolet radiation due to the lasing of an argon-fluoride gas mixture. The last 10 years has seen its development and succesful use in the materials processing industry.

SUMMARY OF THE INVENTION

In general, the invention features a method of administering a therapeutic substance to a human patient, the method having the steps of ablating the stratum corneum of a region of the skin of the patient using pulsed laser light of wavelenth, pulse length, pulse energy, pulse number, and pulse repetition rate sufficient to ablate the stratum corneum without significantly damaging the underlying epidermis, and applying the therapeutic substance to the region of ablation.

In preferred embodiments, the therapeutic substance is a polar compound, a peptide hormone, a non-peptide hormone, a non-hormone peptide or protein, or a gaseous anesthetic; the pulse repetition rate is less than 2 Hz; there is interposed between the skin of the patient and the laser an aperture adapted to limit the laser light illuminating the skin of the patient to the region; each pulse of the laser light removes stratum corneum of a thickness of between 1 and 5 $\mu$m; and ablation comprises the complete and uniform vaporization of tissue.

The methods of the invention are an excellent way of administering percutaneously a large variety of therapeutic substances. The barrier function of the stratum corneum is substantially overcome by laser ablation, which allows for good control of both the depth and extent of the ablation.

DESCRIPTION OF THE PREFERRED EMBODIMENTS

We first briefly describe the drawings.

DRAWINGS

FIG. 1a and FIG. 1b illustrations of a section of skin in which part of the stratum corneum has been removed by laser ablation.

METHODS

Tissue Preparation

Figure 1A:
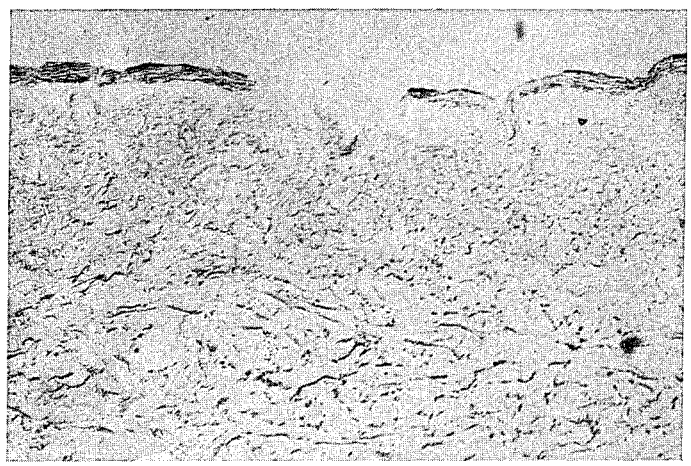

Full thickness human abdominal skin specimens were obtained from autopsy from 17 subjects and equilibrated more than 24 hr at 100% relative humidity at 4° C. The sample population consisted of both male and female Caucasian subjects over a broad range of ages, 30-80 years. Each specimen was Portioned into 8 circular replicate test samples with a 3 cm diameter punch, and each sample was held on a moist paper towel on a glass slide in a 100% relative humidity chamber for about 30 min until used in the laser ablation experiment. Alternate methods for stratum corneum removal from full thickness skin samples were also tested: (i) a 1 cm diameter area was stripped 30 times with adhesive tape, revealing a glistening layer; and (ii) the epidermis was manually removed after mild heat treatment in a 60° C. water bath for 30 seconds. All samples were used for the tritiated water flux experiments.

In separate experiments, isolated stratum corneum was prepared from full thickness abdominal skin samples by (i) mild heat treatment (30 seconds in 60° C. water bath), (ii) manual removal of the epidermis from the dermis, and (iii) trypsin digestion of the adherent viable epidermis by flotation on a 1% trypsinphosphate buffer solution for 1 hr at 24° C. followed by gentle cotton wab abrasion. Such isolated stratum corneum samples were used to estimate the thickness of stratum corneum in the original full thickness samples. A 1.9 cm diameter punched stratum corneum sample was placed on an exposed dermal site on the original autopsy sample during the 24 hr equilibration period. The stratum corneum was then peeled from the dermis, weighed on a Cahn electrobalance (weight =W +D), weighed again after desiccation (weight=D), and thickness (T) calculated: $T=[W/(1 \text{ g/cc})+D/(1.33 \text{ g/cc})]/(2.84 \text{ cm}^2$ area), where W=grams water, D=grams dry stratum corneum, and 1.33 g/cc is the density of dry stratum corneum.

In subsequent studies, paired samples of stratum corneum were either stored in 100% relative humidity for 24 hr or dried over $CaSO_4$ dessicant for 72 hr prior to testing the effect of hydration on the optical absorption coefficient A and the minimum ablation energy threshold $E_{min}$ (room temperature=24° C.).

Laser ablation

The stratum corneum surface of each 3 cm circular test sample was positioned 2 mm behind a thin 3.2 mm diameter Mylar aperture (Dermamask, Hudson Die, Boston, MA) for exposure to an excimer laser beam (model EMG/200, provided by Lambda Physik). The laser used an argon-fluoride gas mixture to yield 193 nm wavelength pulses of 8-20 ns (most preferably 14 ns) duration (full width-half maximum). The energy content of each pulse was measured by replacing the skin sample with an energy meter (Gentech, Canada). The pulse-to-pulse variation in energy content was 10% (SD/mean$\times$100%, n=15). An array of quartz attenuaters positioned at the laser output port allowed control of the pulse energy that reached the skin samples. Each sample from a given specimen was irradiated at the same pulse energy, expressed as the radiant exposure 70, 100, 170, or 480 mJ/cm$^2$ per pulse. The pulse repetition rate did not exceed 2 Hz to avoid unwanted thermal effects due to accumulation of heat in the epidermis. The number of pulses delivered at a particular pulse energy was varied for each of the eight samples. Five 3.2 mm diameter sites were ablated within a 1.5 cm diameter test area on each sample, which corresponded to 22.7% of the total test area. For the 480 mJ/cm$^2$ experiments, nine 2.2 mm diameter sites were ablated, which corresponded to 19.3% of the total test area. After ablation, the samples were evaluated for $^3$H$_2$O permeability enhancement.

Optical absorption coefficients (A) at 193 nm for both wet and dry stratum corneum were determined for both ablative and sub-ablative irradiances. Each sample was placed on the 3.2 mm diameter aperture and a vacuum photodiode detector, calibrated versus the Gentec energy meter, was placed 10 cm behind the sample. Laser pulses at 100 mJ/cm$^2$ were delivered, and the transmission through the sample noted after each pulse. The autofluorescence of the tissue excited by the laser did not register on the detector. Only when the ablation site had penetrated approximately ¾ of the tissue could transmitted light be detected. An attenuator was then placed in the beam path to reduce the radiant exposure to 7 mJ/cm$^2$, which is well below the threshold for ablation, and transmission measurements were made. Alternately, the attenuator was removed, ablative doses delivered and the transmission noted, then the attenuator repositioned for a sub-ablative transmission measurement. This cycle was repeated until the ablation site completely penetrated the stratum corneum, as indicated by shining a flashlight on one side of the sample and observing the first appearance of a pinhole of light against a white card on the other side. The total number of pulses N required to achieve penetration was noted, and the tissue removed per pulse was calculated: d (thickness T)/(N pulses), where $T_{wet}$=28 um and $T_{dry}$=6.3 um. The transmission data were plotted as $y = -\log(\text{transmission}_i/\text{transmission}_N)$, versus x=id where i is the pulse number. The plots were very linear and the slopes specified the absorption coefficients for ablative and subablative irradiances for both wet and dry stratum corneum, according to Beer's law.

The minimal thresholds for ablation of wet and dry isolated stratum corneum samples were determined by delivery of 1000 pulses at a given pulse energy. Below the ablation threshold, no tissue removal was visible. At the threshold, about 400 pulses penetrated the stratum corneum as indicated by appearance of a pinhole.

Diffusion measurements

Eight samples from a given specimen were placed in glass diffusion chambers designed for $^3$H$_2$O flux measurements. The interior diameter of the diffusion chamber was 1.5 cm and was aligned with the 1.5 cm diameter test area of the ablated samples. Both the donor and receptor volumes were filled with 2 ml of normal saline (0.9 g NaCl/100 ml) and stirred continuously. Tritiated water was introduced into the donor volume and 10 ul aliquots from the receptor volume were assayed by liquid scintillation counting over a 48 hr period. The plot of receptor $^3$H$_2$O versus time was linear and the flux was calculated by the slope. This flux of labelled water was treated as due to a donor concentration of 1 g/cc and a receptor concentration of zero g/cc, which allowed the permeability constant $k_p$ to be calculated in units of cm/hr: $k_p$=(flux g/cm$^2$−hr)/(1 g/cc).

Electrical measurements

Electrical measurements were made with stainless steel electrodes inserted into the donor and receptor volumes of the diffusion chamber. Impedance measurements were made from 100 to 300 Hz using a bridge technique and a 1 Volt amplitude sine wave generator. Impedance values varied linearly with frequency over this limited range. The electrode impedance was determined in the saline-filled chamber before insertion of the skin sample, and was treated as a parallel resistance and capacitance in series with a parallel skin resistance and capacitance. The capacitance and conductance of the skin were calculated, normalized by the area of the diffusion chamber, and expressed as the specific resistance in kohms-cm$^2$.

Histology

A full thickness hydrated skin sample was exposed to 140 pulses at 60 mJ/cm$^2$ per pulse through a thin 0.3 mm wide rectangular aperture. The sample was frozen in freezing medium (Tissue-Tek, Miles Scientific) and 10 um sections prepared by microtome. A 20 ul volume of 0.1 N NaOH was applied to the frozen section under a coverslip on a glass microscope slide, which caused the stratum corneum to swell for photography.

Results

Figure 1B:
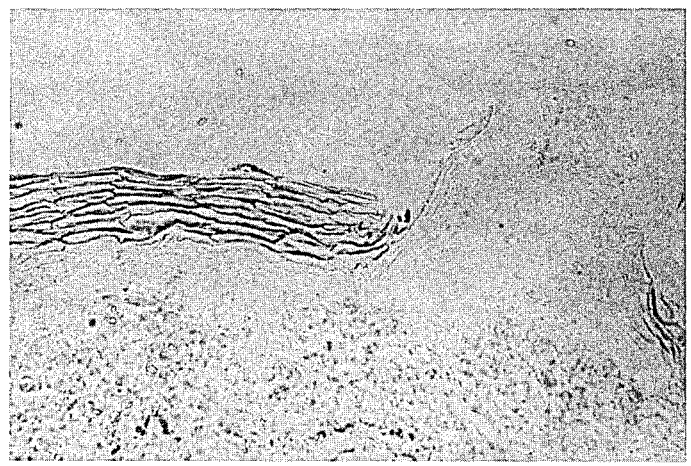
Figure 2:
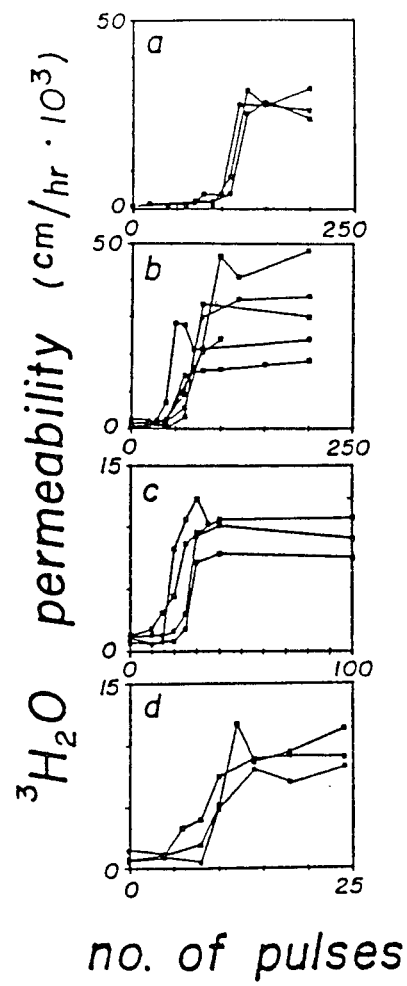
FIG. 2 illustrates the graph from which are obtained the permeability constants for $^3H_2O$ on sections of skin that have had part of the stratum corneum removed by laser ablation with laser pulses of varying radiant exposures.

The removal of stratum corneum by laser ablation is illustrated in the light microscope photographs of a 10 um frozen section of full thickness skin swollen by 0.1 N NaOH, shown in FIG. 1. FIG. 1a is a side view of a skin section in which the bar represents the ablation site. FIG. 1b is a side view of an edge of the ablation site. The stratum corneum has been completely removed from the 0.3 mm wide ablation site by 140 laser pulses at 60 mJ/cm$^2$ per pulse, with minimal penetration into the viable epidermis. Epidermal separation is artificial. Such controlled ablation allows complete removal of the permeability barrier with minimum damage to living tissue. The sharpness of the boundary between intact skin and the ablation site indicates the spatial resolution of the ablation process. The original fully hydrated stratum corneum thickness of the full thickness skin sample was approximately 28.0±1.6 um, based on a dry weight of 0.84±0.08 g/cm$^2$ and a maximum hydration of 72.1±1.6%. Therefore, each pulse removed 28 um/140 pulses=0.20 um of tissue.

The flux of tritiated water through the full thickness skin samples increased dramatically once the stratum corneum barrier had been ablated by laser irradiation. In FIGS. 2a–2d the permeability constant for $^3$H$_2$O is shown for samples that have received an increasing number of laser pulses at radiant exposures of 70, 100, 170, and 480 mJ/cm$^2$ per pulse, respectively. Note the different x and y scales of each figure. As the number of pulses increased, the $^3$H$_2$O permeability constant, $k_p$, at first showed little change, then suddenly increased to a maximum value that indicated the stratum corneum had been completely removed. The threshold number of pulses, N, equired to increase $k_p$ to ½ the maximum value was determined for each sample. Since the increase in the permeability constant was so sharp, this threshold indicated the minimum number of pulses required to achieve complete stratum corneum removal. Only a fraction of the skin area that was tested in the diffusion chamber had been laser ablated; therefore the specific enhancement, SE, of the permeability constant was calculated:

$$SE = [(k_p \text{ test})/(k_p \text{ control}) - 1/f]/f,$$

where f is the fraction of the diffusional test area which was ablated (for example, f=0.227). The specific enhancement indicates the expected increase in the permeability constant if all the diffusional test area had been ablated.

Table 1 summarizes the parameters for the ablation process determined by the tritiated water flux experiments at the various pulse energy densities: (i) N, the threshold number of pulses for complete stratum corneum removal, and (ii) $k_p$, the maximum permeability constant achieved after complete stratum corneum removal over a fraction f of the test area. The other calculated parameters are (iii) d, the tissue removed per laser pulse, and (iv) SE, the specific enhancement of the $^3H_2O$ permeability constant. Also listed are the appropriate data for the control samples (no laser exposure), the tape-stripped samples, and the dermal samples with epidermis removed by mild heat treatment.

Figure 3:
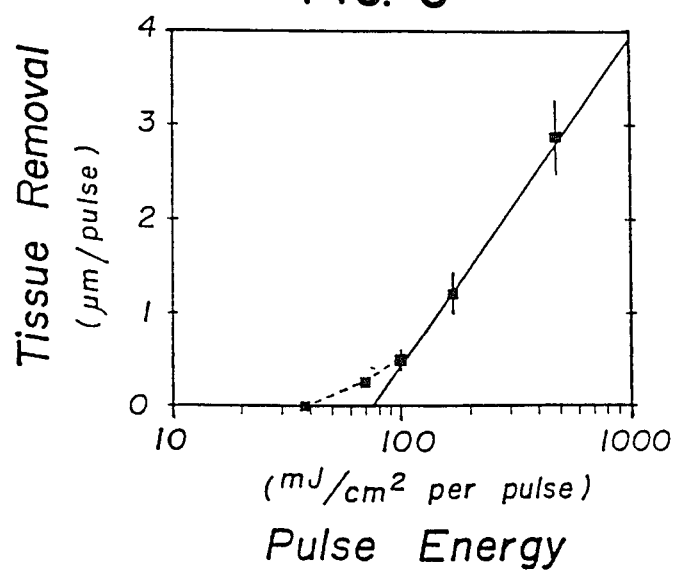
FIG. 3 illustrates the depth of hydrated stratum corneum removed per laser pulse as a function of pulse energy.
Figure 4:
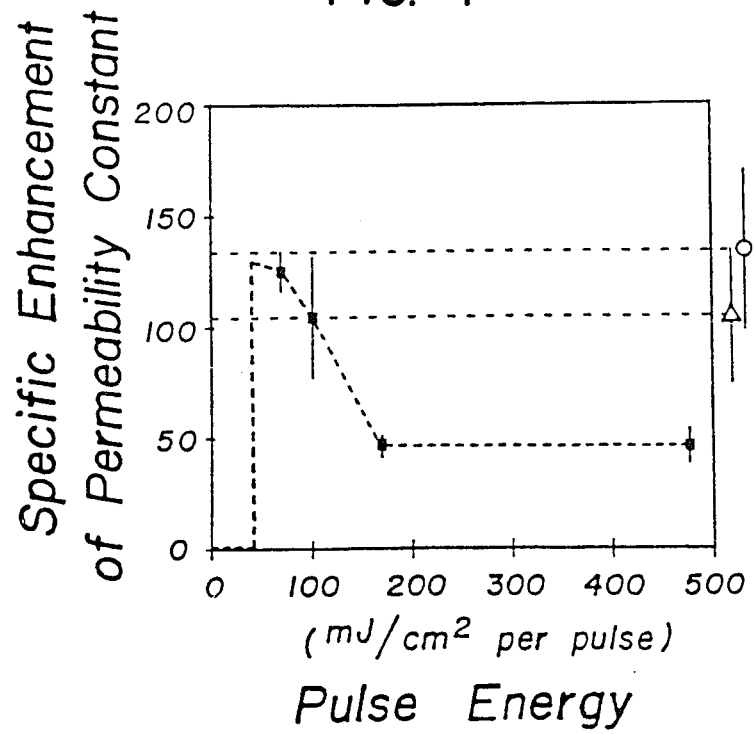
FIG. 4 illustrates the specific enhancement of the $^3H_2O$ permeability constant for full thickness human skin samples after complete removal of the stratum corneum by laser ablation.

The maximum specific enhancement of permeability obtained after complete stratum corneum ablation depended on the pulse energy used in the ablation process, as shown in FIG. 4. The enhancement of permeability was greatest when the pulse energy was less than 100 $mJ/cm^2$ (the dotted line region of FIG. 3). The permeability constant was increased from a control value of $0.95 \times 10^{-3}$ cm/hr to a post-ablation value of $44 \times 10^{-3}$ cm/hr (specific enhancement=124-fold) following complete removal of stratum corneum by pulses at 70 $mJ/cm^2$ per Pulse. As higher pulse energies were used, the maximum permeability constant achieved dropped to $9.7 \times 10^{-3}$ cm/hr (specific enhancement=45-fold). This result suggests that at high pulse energies above 100 $mJ/cm^2$ per pulse, ablation alters the epidermal tissue lining the ablation site in a manner that decreases the diffusion constant for water, as if the laser is sealing the hole. Only the gentle ablation at low pulse energies successfully achieves stratum corneum removal without such epidermal alteration. The 124-fold specific enhancement in permeability achieved by gentle ablation compares favorably with the 132-fold specific enhancement obtained when stratum corneum is removed by adhesive tape stripping (open circle in FIG. 4), and

TABLE 1

| description | E $mJ/cm^2$ | n | N pulses | d um/pulse | $k_p$ cm/hr × $10^3$ | f | SE |
|---|---|---|---|---|---|---|---|
| control | — | 17 | — | — | 0.95 ± 0.45 | 1 | 1-fold |
| s. corneum removed: | | | | | | | |
| by heat tx | — | 3 | — | — | 98 ± 28 | 1 | 103-fold |
| by tape-stripping | — | 3 | — | — | 56 ± 15 | 0.441 | 132-fold |
| by laser ablation: | 70 | 3 | 115 ± 7 | 0.24 | 27 ± 2 | 0.227 | 124-fold |
| | 100 | 7 | 56 ± 10 | 0.50 | 23 ± 6 | 0.227 | 104-fold |
| | 170 | 4 | 23 ± 4.1 | 1.4 | 11 ± 1 | 0.227 | 46-fold |
| | 480 | 3 | 9.7 ± 1.4 | 2.8 | 10 ± 1 | 0.193 | 45-fold |

E—radiant exposure per pulse used for ablation of stratum corneum.
n—number of specimens in means ± std. devs.
N—number of laser pulses required to remove wet stratum corneum (28 um).
d—depth of stratum corneum removed per pulse (28 um/N).
$k_p$—permeability constant for $^3H_2O$ across skin after s. corneum removal.
f—fraction of diffusion test area treated.
SE—specific enhancement = $[(k_p\text{test}/k_p\text{control}) - (1 - f)]/f$.

As the laser pulse energy was increased, fewer pulses were required for complete stratum corneum removal, as shown in FIG. 3. The laser removes 0.24, 0.50, 1.4, and 2.8 um of stratum corneum per pulse at radiant exposures of 70, 100, 170, and 480 $mJ/cm^2$, respectively. The means and standard deviations indicate the specimen-to-specimen variation. Above 100 $mJ/cm^2$ pulse energies, rapid ablation occurs and the tissue removed per pulse is linearly related to the logarithm of the pulse energy used for ablation. The x-axis intercept of this linear portion of the graph indicates the threshold radiant exposure $E_{th}$ for rapid ablation equals 72.4 $mJ/cm^2$ per pulse, and the reciprocal slope, the effective optical absorption coefficient A, is 6640 $cm^{-1}$ during ablation. Below 100 $mJ/cm^2$ the tissue removal is less vigorous (dotted line), and the removal rate no longer conforms to the linear relationship. The actual minimum energy for ablation $E_{min}$ is about 38±2 $mJ/cm^2$, for both wet and dry stratum corneum.

with the 103-fold specific enhancement obtained by removal of the upper epidermis after mild thermal treatment (open triangle in FIG. 4).

Table 2 summarizes the results for experiments on both wet and dry isolated stratum corneum samples. The optical absorption coefficient A for hydrated isolated stratum corneum was 5490 $cm^{-1}$ at ablative irradiances and 6460 $cm^{-1}$ at sub-ablative irradiances. These values are similar, and agree well with the 6640 $cm^{-1}$ value for A obtained by 1/slope in FIG. 3 of the $^3H_2O$ flux experiments. For the dry samples, the ablative and sub-ablative absorption coefficients were 23410 $cm^{-1}$ and 21180 $cm^{-1}$ respectively. At 100 $mJ/cm^2$ the dry samples required 63.0 ±4.7 (n=5) pulses, and the wet samples required 60.3 ±9.1 (n=3) pulses for ablation to penetrate the stratum corneum. The hydration of the tissue does not affect the threshold number of laser pulses required to penetrate the stratum corneum.

TABLE 2

| description | W $mg/cm^2$ | H hydration | t thickness | $^3H_2O$ flux expts. A $cm^{-1}$ | optical transmission expts. A $cm^{-1}$ | ablation threshold $E_{th}$ $mJ/cm^2$ |
|---|---|---|---|---|---|---|
| dry stratum corneum | 0.84 ± 0.8 (7) | 0% | 6.3 um | — | 24000 | 38 |

TABLE 2-continued

| description | W mg/cm$^2$ | H hydration | t thickness | $^3$H$_2$O flux expts. A cm$^{-1}$ | optical transmission expts. A cm$^{-1}$ | ablation threshold $E_{th}$ mJ/cm$^2$ |
|---|---|---|---|---|---|---|
| wet stratum corneum | 3.0 ± 0.2 (7) | 72.1 ± 1.6% | 28. um | 6600 | 6000 | 38 | means ± std. devs. (n)
W—weight of stratum corneum per unit area (mg/cm$^2$).
H—hydration expressed as (g water)/(g total weight) × 100%.
t—stratum corneum thickness calculated from wet and dry weights.
A—optical absorption coefficient at 193 nm.
$E_{th}$—threshold pulse radiant exposure for ablation.

Figure 5:
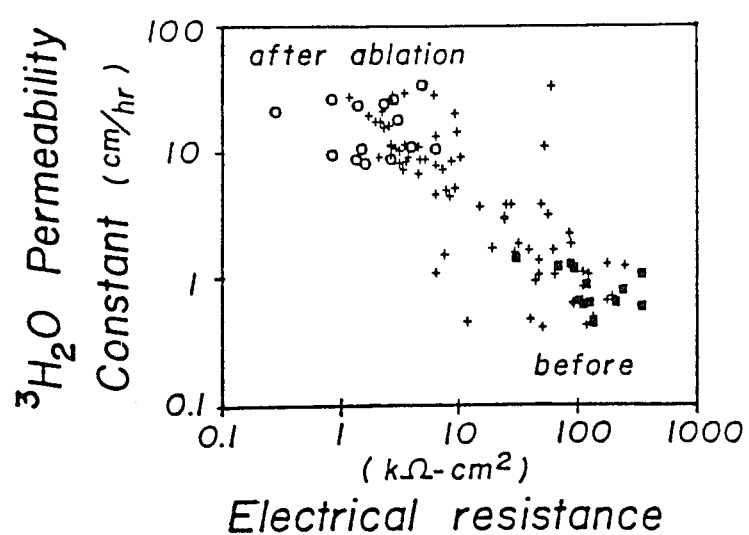
FIG. 5 illustrates the correlation of $^3H_2O$ permeability and electrical resistance for full thickness human skin samples after different degrees of stratum corneum removal by laser ablation.

The electrical resistance and capacitance of the skin samples were also measured during the $^3$H$_2$O diffusion experiments (100–300 Hz). The electrical resistance dropped suddenly when the $^3$H$_2$O permeability constant increased suddenly, as in FIGS. 3a–3d. The electrical capacitance dropped more gradually with increasing ablation, and reached a minimum after complete ablation. The correlation between $^3$H$_2$O permeability constant and electrical resistance is shown in FIG. 5. For each tissue specimen, the control sample value is shown as a solid box, and the value for the sample receiving the maximum number of laser pulses is shown as an open circle. All other measurements for samples receiving various numbers of laser pulses at various pulse energies are shown as crosses. Note how the data cluster into two distinct locations on this correlation plot. The initial control values for resistance were in the range of 130±30 kohm-cm$^2$. Once a threshold number of pulses had been delivered, the electrical resistance dropped suddenly to an intermediate value of about 10 kohms-cm$^2$ and the $^3$H$_2$O permeability constant jumped to its maximum value. Further ablation dropped the electrical resistance to the final range of 1.2 ±0.5 kohms-cm$^2$. Once electrical resistance had dropped to less than 5 kohms-cm$^2$, there was high confidence that the maximum permeability had been attained.

Operational Theory

The parameter which allows controlled, precision removal of tissue by a pulsed laser is a very large optical absorption coefficient A, where 1/A is the 1/e depth of penetration of radiant energy into the tissue. Only when 1/A is on the order of micrometers can one remove small incremental volumes of tissue with each laser pulse. There are two wavelength regions where optical absorption is sufficiently large to meet this condition: (i) in the very short ultraviolet (e.g., 198 nm) where there is strong absorption by the tissue protein, and (ii) in the near infrared (e.g., 2940 nm, provided by the Er:YAG laser) where there is strong absorption by the tissue water. For ablation of dry tissue such as stratum corneum, the 193 nm wavelength which is absorbed by protein rather than water is best.

When absorption is stronger than scattering, the optics of radiant energy transmission can be discussed in terms of Beer's law: $E(x) = E_o e^{-Ax}$, where $E_o$ is the incident radiant exposure in mJ/cm$^2$, and E(x) is the radiant exposure at a depth x. Assume that a threshold radiant exposure $E_{th}$ (mJ/cm$^2$ per pulse) is required to cause tissue ablation. The depth of ablation is specified: $x1 = (a/A)\ln(E_0/E_{th})$. This expression can be rearranged to allow plotting FIG. 3:

$$x_{ab1} = A\ln(E_o) - A\ln(E_{th})$$

On the x-axis is Plotted the logarithm of the pulse radiant exposure $\ln(E_o)$ and on the y=axis is plotted the volume of tissue removed per pulse $x_{ab1}$, expressed as um/pulse per cm$^2$ skin surface. Such a plot is linear, as shown in FIG. 3, at higher pulse energies. The optical absorption A that is effective during the ablation process is specified by the reciprocal slope of this line, which is 6640 cm$^{-1}$ (1/e=1.5 um). This value agrees well with the optical absorption coefficients measured by the transmission experiments at both ablative and subablative pulse energies. The x-axis intercept occurs at the apparent threshold pulse energy $E_{th}$ of 72.4 mJ/cm$^2$ for ablation, which is consistent with the Beer's law theory. This value implies that the radiant energy density required for ablation is $A \times E_{th} = 481$ J/cc, which characterizes the ablation process at high pulse energies for fully hydrated stratum corneum. Since the initial tissue temperature was 22° C., the 481 J/cc would be sufficient to raise the temperature to 136° C., which is above the boiling point of water. An apparent threshold temperature of 123° C. has been reported for clinical purpura caused by pulsed tunable dye laser irradiation at 577 nm, which was attributed to a mechanism of explosive vaporization. Consider that 2560 J/cc are required to completely vaporize pure water initially at 22° C. Therefore, the energy density 481 J/cc for ablation of hydrated stratum corneum, which is 72% water, is sufficient to vaporize only 26% of the tissue water. These calculations suggest that at the higher pulse energies above 100 mJ/cm$^2$ most of the tissue is being removed as particulate matter by an explosive event, as opposed to complete and uniform vaporization of the tissue.

At pulse energies below 100 mJ/cm$^2$ a different mechanism of tissue removal is operating, since the rate of tissue removal departs from the simple Beer's law theory described above (dotted line in FIG. 3). The simple theory of explosive vaporization would predict no ablation should occur below 72.4 mJ/cm$^2$, yet ablation can be observed at pulse energies as low as $E_{min} = 38$ mJ/cm$^2$ per pulse. A theory of photochemical breakdown of polymers which yields a cool, non-thermal ablation has been proposed for ablation at low pulse energies.

The degree of control and the magnitude of enhancement demonstrated in these experiments are very encouraging for both clinical and research applications. There are two modes of operation suggested by these results: (i) gentle ablation at low pulse energies below 72.4 mJ/cm$^2$ per pulse, and (ii) rapid ablation at high pulse energies above 100 mJ/cm$^2$. The control attainable is about 0.24 ±0.02 um/pulse for gentle ablation (70 mJ/cm$^2$), and about 2.9 ±0.5 um/pulse for rapid ablation (480 mJ/cm$^2$). The minimum threshold for ablation occurs at 38 mJ/cm$^2$, which requires about 400 pulses to penetrate both wet and dry stratum corneum. These values would imply the minimum unit of tissue removal is 0.08 um/pulse for wet tissue and 0.02 um/pulse for dry tissue; however, pulse-to-pulse variation in energy and the spatial uniformity of the laser beam become limiting factors that complicate attempts to specify the minimum unit of ablation. Gentle ablation achieves the maximum enhancement of permeability, similar to that obtained with tape stripping, and avoids the epidermal alterations seen at higher pulse energies, which lower the enhancement of $^3H_2O$ permeability. Nevertheless, rapid ablation still achieves good results.

Use

The stratum corneum of a patient is removed by laser ablation. The therapeutic compound to be administered (or a suitable solution, paste, etc. containing it) is then placed on the region of stratum corneum removal. The absence of the barrier function attributable to the stratum corneum enhances percutaneous transport of the therapeutic compound.

The method of the invention can be used for percutaneous transport of a variety of therapeutic compounds, for example, nitroglycerin, and antinauseants such as scopolamine; antibiotics such as tetracycline, streptomycin, sulfa drugs, kanamycin, neomycin, penicillin, and chloramphenicol; and various hormones, such as parathyroid hormone, growth hormone, gonadotropins, insulin, ACTH, somatostatin, prolactin, placental lactogen, melanocyte stimulating hormone, thyrotropin, parathyroid hormone, calcitonin, enkephalin, and angiotensin. The therapeutic compounds can be administered as one dose or in a timed-release fashion, i.e., an amount of the therapeutic compound sufficient for an extended period of time is applied to the ablated region such that it is gradually transported through the ablation over time as needed.

The method of the invention provides an excellent way to administer percutaneously polar or high molecular weight compounds that normally do not readily penetrate the stratum corneum. Gaseous anesthetics, such as, for example, vaporized diethyl ether, can also be administered by the methods of the invention by exposing the region of stratum corneum ablation to the vapor.

Other Embodiments

Other embodiments are within the following claims. For example, the method of the invention can be used for blood gas monitoring.

We claim:

1. A method of facilitating percutaneous transport by overcoming the barrier function of the stratum corneum, said method comprising
    ablating the stratum corneum of a region of the skin of said patient using pulsed laser light of wavelength, pulse length, pulse energy, pulse number, and pulse repetition rate sufficient to ablate said corneum without significantly damaging the underlying epidermis.

2. The method of claim 1 wherein said pulse repetition rate is less than 2 Hz.

3. The method of claim 1 wherein there is interposed between the skin of said patient and said pulsed laser light an aperture adapted to limit the laser light illuminating the skin of said patient to said region.

4. The method of claim 1, wherein said pulsed laser light is near infrared.

5. The method of claim 1, wherein said pulsed laser light has a pulse energy equal to or less than 170 mJ/cm$^2$ per pulse.

6. The method of claim 5, wherein said pulse energy is equal to or less than 100 mJ/cm$^2$ per pulse.

7. The method of claim 1, further comprising the step of applying a therapeutic substance to said region of ablation.

8. The method of claim 7 wherein said therapeutic substance comprises a polar compound, a peptide hormone, a non-peptide hormone, a non-hormone peptide or protein, or a gaseous anesthetic.

* * * * *

UNITED STATES PATENT AND TRADEMARK OFFICE
CERTIFICATE OF CORRECTION

PATENT NO. : 4,775,361

DATED : October 4, 1988

INVENTOR(S) : Steven L. Jacques et al.

It is certified that error appears in the above-identified patent and that said Letters Patent is hereby corrected as shown below:

Col. 2, line 14, "was Portioned" should be --was portioned--;

Col. 2, line 32, "wab" should be --swab--;

Col. 4, line 63, "equired" should be --required--;

Col. 5, line 55, "reciProcal slope" should be --reciprocal slope--;

Col. 7, line 29, "resistance" is misspelled;

Col. 7, line 61, "x1=(a/A)" should be --$x_{abl}=(a/A)$--;

Col. 7, line 65, "Plotted" should be --plotted--.

Signed and Sealed this

Twenty-fifth Day of April, 1989

Attest:

DONALD J. QUIGG

Attesting Officer

Commissioner of Patents and Trademarks